US007767683B2

(12) United States Patent
Lopez de Diego et al.

(10) Patent No.: US 7,767,683 B2
(45) Date of Patent: Aug. 3, 2010

(54) HYDROGEN SUCCINATE SALTS OF TRANS-4-((1R, 3S)-6-CHLORO-3-PHENYLINDAN-1-YL)-1,2,2-TRIMETHYLPIPERAZINE AND THE USE AS A MEDICAMENT

(75) Inventors: Heidi Lopez de Diego, Naerum (DK); Ole Nielsen, Valby (DK); Lone Munch Ringgard, Roskilde (DK); Henrik Svane, Virum (DK); Allan Carsten Dahl, Nyrup (DK); Mark Howells, Copenhagen S (DK); Benny Bang-Andersen, Copenhagen S (DK); Lars Ole Lyngso, Vekso Sj (DK); Sherry Lynn Collier, Flemington, NJ (US)

(73) Assignee: H. Lundbeck A/S, Valby-Copenhagen (DK)

( * ) Notice: Subject to any disclaimer, the term of this patent is extended or adjusted under 35 U.S.C. 154(b) by 96 days.

(21) Appl. No.: 10/568,572

(22) PCT Filed: Aug. 18, 2004

(86) PCT No.: PCT/DK2004/000545

§ 371 (c)(1),
(2), (4) Date: Aug. 14, 2006

(87) PCT Pub. No.: WO2005/016900

PCT Pub. Date: Feb. 24, 2005

(65) Prior Publication Data

US 2006/0281759 A1 Dec. 14, 2006

Related U.S. Application Data

(60) Provisional application No. 60/496,058, filed on Aug. 18, 2003, provisional application No. 60/520,246, filed on Nov. 14, 2003.

(30) Foreign Application Priority Data

Aug. 18, 2003 (DK) ............................ 2003 01180
Sep. 11, 2003 (DK) ............................ 2003 01305

(51) Int. Cl.
*A61K 31/495* (2006.01)
*C07D 241/04* (2006.01)
(52) U.S. Cl. ................................ 514/255.03; 544/403
(58) Field of Classification Search ................ None
See application file for complete search history.

(56) References Cited

U.S. PATENT DOCUMENTS

| 4,443,448 A * | 4/1984 | Bogeso .............. 514/254.02 |
| 6,410,794 B1 | 6/2002 | Zinnen et al. |
| 6,444,854 B1 | 9/2002 | Dapremont et al. |
| 6,455,736 B1 | 9/2002 | Zinnen et al. |
| 6,506,940 B1 | 1/2003 | Jadav et al. |

FOREIGN PATENT DOCUMENTS

| EP | 0 638 073 B1 | 6/2000 |
| WO | WO 93/08799 | 5/1993 |
| WO | 95/15299 A1 | 6/1995 |
| WO | 2005/016901 A1 | 2/2005 |

OTHER PUBLICATIONS

Robichaud et al. in Annual Reports in Medicinal Chemistry, vol. 36, pp. 11-20 (2000).*
Zhang et al. Expert Opin.Ther.Patents, vol. 16,p. 587-630 (2006).*
Gonzalez-Gomez et al. Bioorganic & Medicinal Chemistry Letters, vol. 13, pp. 175-178 (2003).*
Newman Exp.Opin.Ther.Patents, vol. 10, pp. 1095-1122 (2000).*
Willner, P. Dopamine and Depression: A Review of Recent Evidence. II. Theoretical Approaches. Brain Res. Rev. 1983. 6(3):225-236.
Willner, P. Dopamine and Depression: A Review of Recent Evidence. III. The Effects of Antidepressant Treatments. Brain Res. Rev. 1983, 6(3):237-246.
Klaus P. Bogeso, et al., "Enhanced D1 Affinity in a Series of Piperazine Ring Substituted 1-Piperazino-3-Arylindanes with Potential Atypical Antipsychotic Activity", Journal of Medicinal Chemistry, vol. 38, No. 22, 1995, pp. 4380-4392.
Froimowits, et al., J. Med. Chem. 2000, 43, 4981-4992.
Bogeso J. Med. Chem., 1985, 28, 1817-1828.
Klaus P. Bøgesø, Drug Hunting: The Medicinal Chemistry of 1-Piperazino-3-Phenylindans and Related Compounds, Viborg, Denmark: Nørhaven (1998). pp . 1-144.
Klaus P. Bøgesø, "Neuroleptic Activity and Dopamine-Uptake Inhibition in 1-Piperazino-3-phenylindans," J. Med. Chem. 26(7): 935-47 (1983).
Derek N. Eder, "CEE-03-310 CeNeS Pharmaceuticals," Curr. Op. Invest. Drugs. 3(2): 284-88 (2002).
Mark J. Millan et al., "S18327 (1-{2-[4-(6-Fluoro-1,2-benzisoxazol-3-yl)piperid-1-yl]ethyl}3-phenyl imidazolin-2-one), a Novel, Potential Antipsychotic Displaying Marked Antagonist Properties at α2-Adrenergic Receptors: I. Receptorial, Neurochemical, and Electrophysiological Profile," J. Pharmacol. Exp. Ther. 292(1): 38-53 (2000).
Vagn Pedersen and Klaus Bøgesø, "Drug Hunting," In Interviews by David Healy, The Psychopharmacologists II, pp. 561-579, London: Arnold (1999).
Philip Seeman, Science & Medicine, "Dopamine Receptors and Psychosis," Sci. Amer. 28-37 (Sep./Oct. 1995).

(Continued)

*Primary Examiner*—Emily Bernhardt
(74) *Attorney, Agent, or Firm*—Stephen G. Kalinchak; Margaret M. Buck (57) ABSTRACT

4-((1R,3S)-6-Chloro-3-phenylindan-1-yl)-1,2,2-trimethylpiperazine hydrogen succinate, pharmaceutical compositions containing the salt and the medical use thereof, including for the treatment of schizophrenia and other psychotic disorders. Also described are methods for the preparation of 4-((1R,3S)-6-Chloro-3-phenylindan-1-yl)-1,2,2-trimethylpiperazine and medical uses thereof.

12 Claims, 3 Drawing Sheets

OTHER PUBLICATIONS

Michael Bech Sommer et al., "Application of (2-Cyanoaryl)arylacetonitriles in Cyclization and Annulation Reactions. Preparation of 3-Arylindans, 4-Aryl-3,4-dihydronaphthalenes, 4-Arylisoquinolines, 1-Aminonaphthalenes, and Heterocyclic Analogues," J. Org. Chem. 55(16): 4822-27 (1990).

Paul Willner, "Dopamine and Depression: A Review of Recent Evidence. I. Empirical Studies." Brain Res. Rev. 6: 211-24 (1983).

Clark, William M. et al., "A Catalytic Enantioselective Synthesis of the Endothelin Receptor Antagonists SB-209670 and SB-217242. A Base-Catalyzed Stereospecific Formal 1,3-Hydrogen Transfer of a Chiral 3-Arylindenol", J. Am. Chem. Soc. 1998, 120:4550-4551.

Clark, William M. et al., "A Highly Enantioselective Conjugate Reduction of 3-Arylinden-1-ones Using Bakers' Yeast for the Preparation of (S)-3-Arylindan-1-ones", Organic Letters 1999, 1(11):1839-1842.

Yun, Jaesook et al., "Efficient Kinetic Resolution in the Asymmetric Hydrosilylation of Imines of 3-Substituted Indanones and 4-Substituted Tetralones", J. Org. Chem. 2000, 65(3):767-774.

Haleblian, John, et al., "Pharmaceutical Applications of Polymorphism", Journal of Pharmaceutical Sciences, Aug. 1969, pp. 911-929, vol. 58, No. 8.

Davies, Huw M. L., et al., "Asymmetric Synthesis of (+)-Indatraline Using Rhodium-Catalyzed C-H Activation", Tetrahedron Letters, 2002, pp. 4951-4953, 43, Pergamon.

Balsara, J. J, et al. Effect of Drugs Influencing Central Serotonergic Mechanisms on Haloperidol-Induced Catalepsy. Psychopharmacol. 1979. 62:67-69.

Carlsson, A. Antipsychotic Drugs, Neurotransmitters, and Schizophrenia. Am. J. Psych. 1978 135(2):164-173.

Carlsson, L. et al. QTU-Prolongation and Torsades de Pointes Induced by Putative Class III Antiarrhythmic Agents in the Rabbit: Etiology and Interventions. J. Cardiovasc. Pharmacol. 1990. 16:276-285.

Chauret, N. et al. The Use of 3-[2-(N,N-Diethyl-N-Methylammonium)Ethyl]-7-Methoxy-4-Methylcoumarin (AMMC) as a Specific CYP2D6 Probe in Human Liver Microsomes. Drug Metab. Dispos. 2001. 29(9):1196-1200.

Hyttel, J. et al. Neurochemical Profile of Lu 19-005, a Potent Inhibitor of Uptake of Dopamine, Noradrenaline, and Serotonin. J. Neurochem. 1985 44:1615-1622.

GR Desiraju, "Cryptic crystallography." Nature Materials. 1 (Oct. 2002) 77-79.

SL Price, "The computational prediction of pharmaceutical crystal structures and polymorphism." Adv. Drug Delivery Rev. 56 (2004) 301-319.

University of Cambridge, "Major advances made in predicting crystal structures." Physics-Condensed Matter. (Nov. 26, 2007); available on line at www.physorg.com/pring1153104.

* cited by examiner

HYDROGEN SUCCINATE SALTS OF TRANS-4-((1R, 3S)-6-CHLORO-3-PHENYLINDAN-1-YL)-1,2,2-TRIMETHYLPIPERAZINE AND THE USE AS A MEDICAMENT

This application is a §371 national stage of PCT International Application No. PCT/DK2004/000545, filed Aug. 18, 2004 on behalf of H. Lundbeck A/S, which claims priority of Danish Application No. PA 200301180, filed Aug. 18, 2003 and Danish Application No. PA 200301305, filed Sep. 11, 2003, and claims benefit of U.S. Provisional Application No. 60/496,058 filed Aug. 18, 2003 and U.S. Provisional Application No. 60/520,246 filed Nov. 14, 2003, the contents of all of which are hereby incorporated by reference into the subject application.

The present invention relates to 4-((1R,3S)-6-chloro-3-phenylindan-1-yl)-1,2,2-trimethylpiperazine, in particular the hydrogen succinate and the hydrogen malonate salts thereof, methods for the preparation of 4-((1R,3S)-6-chloro-3-phenylindan-1-yl)-1,2,2-trimethylpiperazin and the salts thereof, pharmaceutical compositions containing these salts and the medical use thereof, including treatment of schizophrenia or other diseases involving psychotic symptoms.

BACKGROUND OF THE INVENTION

The compound, which is the subject of the present invention [4-((1R,3S)-6-chloro-3-phenylindan-1-yl)-1,2,2-trimethylpiperazine] has the general formula (I):

(I)

and is described generically in EP 638 073.

EP 638 073 covers a group of trans isomers of 3-aryl-1-(1-piperazinyl)indanes substituted in the 2- and/or 3-position of the piperazine ring. The compounds are described as having high affinity for dopamine $D_1$, and $D_2$ receptors and the 5-$HT_2$ receptor and are suggested to be useful for treatment of several diseases in the central nervous system, including schizophrenia. EP 638 073 does not disclose the specific enantiomeric form of the above compound of formula (I), only trans isomers in the form of racemates are described.

The enantiomer of formula (I) above has been described by Bøgesø et al. in J. Med. Chem., 1995, 38, page 4380-4392, in the form of the fumarate salt, see table 5, compound (−)-38. This publication concludes that the (−)-enantiomers of compound 38 is a potent $D_1/D_2$ antagonists showing some $D_1$ selectivity in vitro while in vivo it is equipotent as $D_1$ and $D_2$ antagonist. The compound is also described as a potent 5-$HT_2$ antagonist and as having high affinity for $\alpha_1$ adrenoceptors. It is also mentioned that the compound does not induce catalepsy in rats.

The corresponding racemate as well as the fumarate salt of the above compound of formula (I) is also described by Klaus P. Bøgesø in "Drug Hunting, the Medicinal Chemistry of 1-Piperazino-3-phenylindans and Related Compounds", 1998, ISBN 87-88085-10-4 (cf. e.g. compound 69 in table 3, p47 and in table 9A, p101).

Thus, the compound of formula (I) is a mixed $D_1/D_2$ antagonists, a 5-$HT_2$ antagonist and it has also affinity for $\alpha_1$ adrenoceptors. In the following is outlined the possible linkage between different diseases and the dopamine $D_1$ and $D_2$ receptors, the 5-$HT_2$ receptors and the $\alpha_1$ adrenoceptors, respectively.

The aetiology of schizophrenia is not known, but the dopamine hypothesis of schizophrenia (Carlsson, Am. J. *Psychiatry* 1978, 135, 164-173), formulated in the early 1960s, has provided a theoretical framework for understanding the biological mechanisms underlying this disorder. In its simplest form, the dopamine hypothesis states that schizophrenia is associated with a hyperdopaminergic state, a notion which is supported by the fact that all antipsychotic drugs on the market today exert some dopamine $D_2$ receptor antagonism (Seeman *Science and Medicine* 1995, 2, 28-37). However, whereas it is generally accepted that antagonism of dopamine $D_2$ receptors in the limbic regions of the brain plays a key role in the treatment of positive symptoms of schizophrenia, the blockade of $D_2$ receptors in striatal regions of the brain causes extrapyramidal symptoms (EPS). As described in EP 638 073 a profile of mixed dopamine $D_1/D_2$ receptor inhibition has been observed with some so-called "atypical" antipsychotic compounds, in particular with clozapine, used in treatment of schizophrenic patients.

Central $\alpha_1$ antagonistic actions has also been suggested to contribute in improving antipsychotic properties (Millan et al, *JPET,* 2000, 292, 38-53).

Further, selective $D_1$ antagonists have been connected to treatment of sleep disorders and alcohol abuse (D.N.Eder, *Current Opinion in Investigational Drugs,* 2002 3(2):284-288).

Dopamine may also play an important role in the etiology of affective disorders (P. Willner, *Brain. Res. Rev.* 1983, 6, 211-224, 225-236 and 237-246; J. Med. Chem., 1985, 28, 1817-1828).

In EP 638 073 is described how compounds having affinity for 5-$HT_2$ receptors, in particular 5-$HT_2$ receptors antagonists, have been suggested for treatment of different diseases, such as schizophrenia including the negative symptoms in schizophrenic patients, depression, anxiety, sleep disturbance, migraine attacks and neuroleptic-induced parkinsonism. 5-$HT_2$ receptor antagonism has also been suggested to reduce the incidence of extrapyramidal side effects induced by classical neuroleptics (Balsara et al. *Psychopharmacology* 1979, 62, 67-69).

DETAILED DESCRIPTION OF THE INVENTION

Salts of the Invention

It has now been found that the aqueous solubility of the hydrogen succinate salt and of the hydrogen malonate salt of the compound of formula (I) is considerably larger than the aqueous solubility of the corresponding fumarate salt.

As used herein the term "hydrogen succinate" salt of the compound of formula (I) refers to the 1:1 salt of the compound of formula (I) and succinic acid.

As used herein the term "hydrogen malonate" salt of the compound of formula (I) refers to the 1:1 salt of the compound of formula (I) and malonic acid.

The hydrogen succinate salt was found to be more stable than the fumarate salt and than the hydrogen malonate salt and to be non-hygroscopic.

The hydrogen malonate salt of Compound I was found to have a stability similar to the fumarate salt when exposed to light and more stable when exposed to 60° C./80% relative humidity (RH), but less stable than the fumarate salt at 90° C. 90° C. is however a very stressed condition, and does not necessarily relate to stability at normal conditions. The malonate absorbs gradually up to 1% of water when the relative humidity is raised to 95%, but with no hysterhesis. It is therefore considered as non-hygroscopic, but with good wetting properties, which indicates favourable dissolution properties.

The invention also covers crystalline salts of the invention, including, e.g. anhydrates hydrates, and solvates of the salts of the invention. By the term anhydrate is meant the salts of the invention containing no crystal bound water. By hydrates is meant the salts of the invention containing crystal bound water molecules. Hydrates are usually prepared by formation of the salt in presence of some water. By solvates is meant the salts of the invention containing crystal bound solvent molecules. Solvates are usually prepared by formation of the succinate salt in presence of the solvent. The solvent molecules in a single solvate may be of one or two or more different solvents. A solvate may comprise water as one of two or more organic solvents or be only a non-water solvent.

One embodiment of the invention relates to the 1:1 salt of trans-4-((1R,3S)-6-Chloro-3-phenylindan-1-yl)-1,2,2-trimethylpiperazine, i.e. of the compound of formula (I), and succinic acid in the form of a crystalline anhydrate.

The inventors have discovered 2 crystalline forms of the hydrogen succinate salt of Compound I (named alpha and beta).

Figure 1:
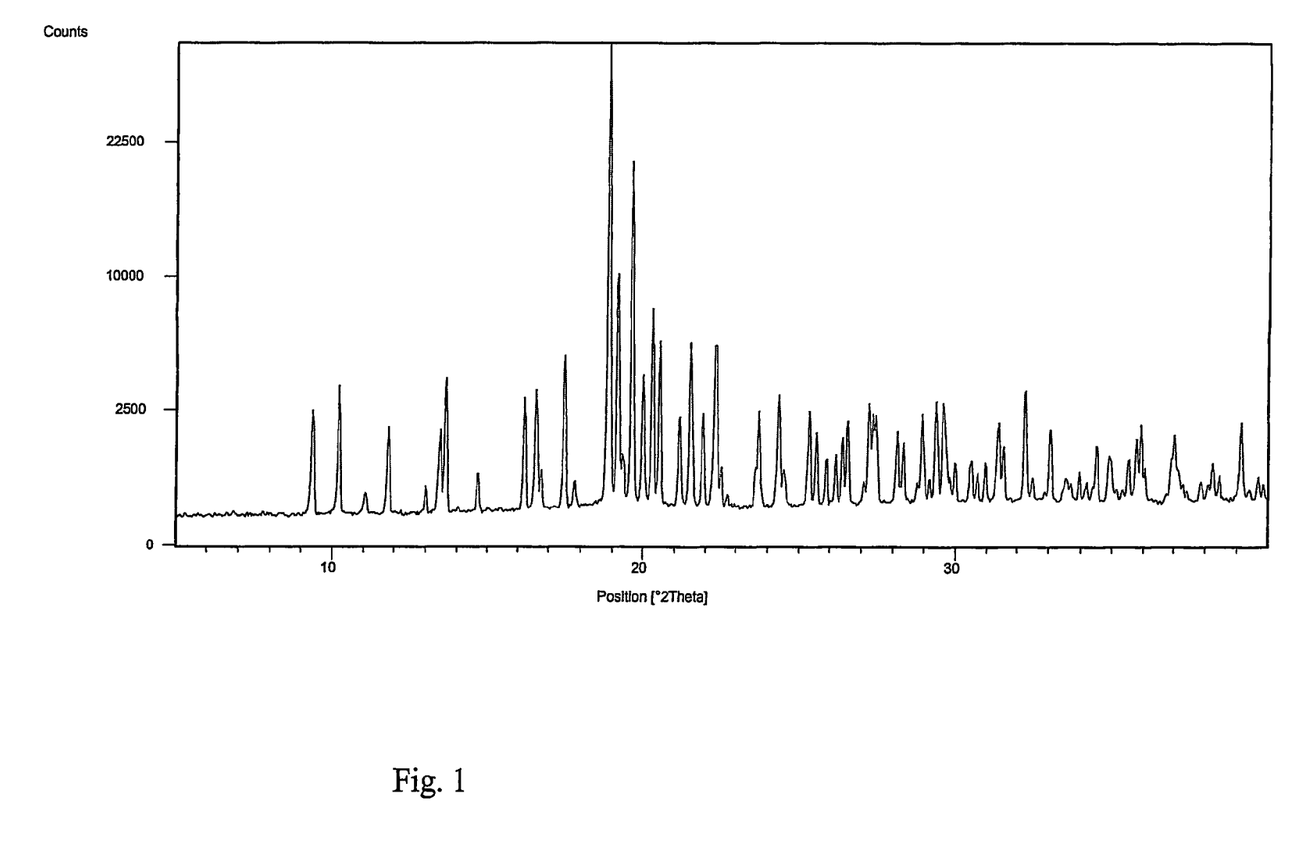
FIG. 1: Shows an X-ray powder diffractogram of the crystalline form alpha of the hydrogen succinate salt of Compound I (obtained using copper $K_{\alpha 1}$ radiation ($\lambda$=1.5406 Å))

Thus, one embodiment relates to a crystalline form of the hydrogen succinate salt of Compound I, which form is named alpha and characterized by one or more of:
(i) an X-Ray powder diffractogram as shown in FIG. 1;
(ii) an X-Ray powder diffractogram pattern as illustrated in Table I obtained using copper $K_{\alpha 1}$ radiation ($\lambda$=1.5406 Å) which shows main peaks at the 2θ-angles given;
(iii) having a DSC (Differential Scanning Calorimetry) trace which shows an endotherm with onset 139-141° C.

Figure 2:
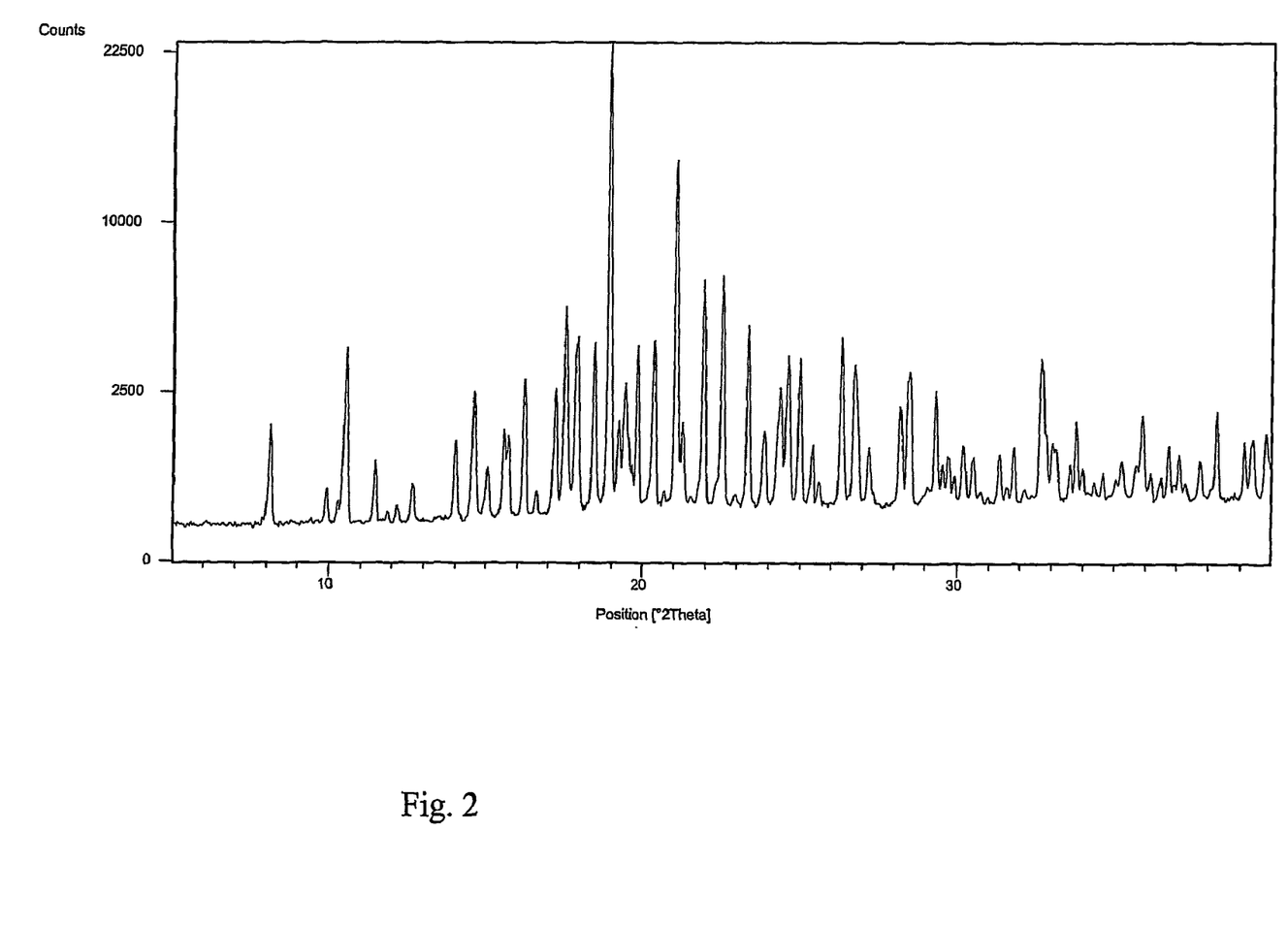
FIG. 2: Shows an X-ray powder diffractogram of the crystalline form beta of the hydrogen succinate salt of Compound I (obtained using copper $K_{\alpha 1}$ radiation ($\lambda$=1.5406 Å))

A further embodiment relates to a crystalline form of the hydrogen succinate salt of Compound I, which form is named beta and characterized by one or more of:
(i) an X-Ray powder diffractogram as shown in FIG. 2;
(ii) an X-Ray powder diffractogram pattern as illustrated in Table I obtained using copper $K_{\alpha 1}$ radiation ($\lambda$=1.5406 Å) which shows main peaks at the 2θ-angles given;
(iii) having a DSC trace which shows an endotherm with onset 135-138° C.

Figure 3:
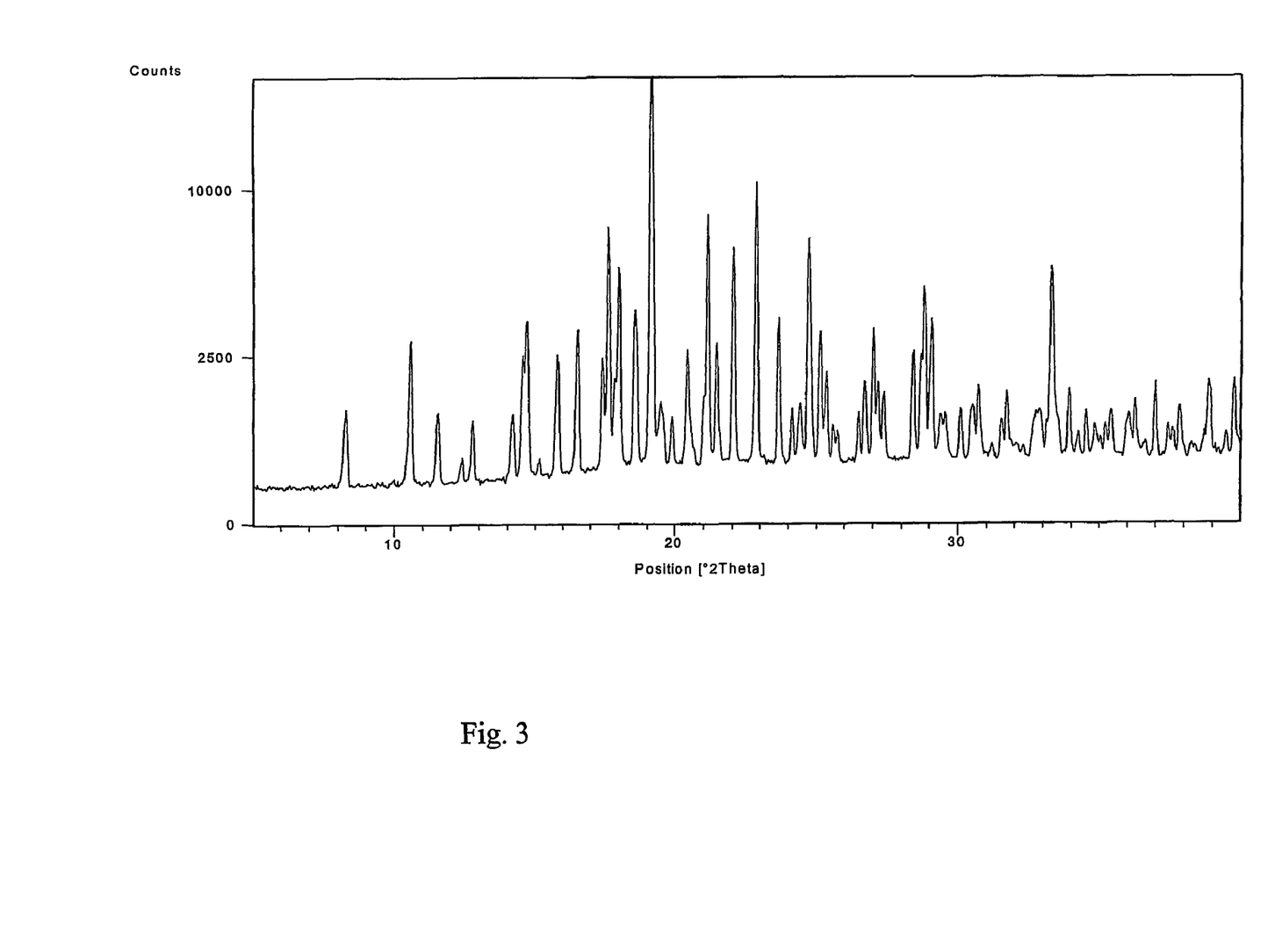
FIG. 3: Shows an X-ray powder diffractogram of the hydrogen malonate salt of Compound I (obtained using copper $K_{\alpha 1}$ radiation ($\lambda$=1.5406 Å)).

A further embodiment relates to a crystalline hydrogen malonate salt of Compound I characterized by one or more of:
(i) an X-Ray powder diffractogram as shown in FIG. 3;
(ii) an X-Ray powder diffractogram pattern as illustrated in Table I obtained using copper $K_{\alpha 1}$ radiation ($\lambda$=1.5406 Å) which shows main peaks at the 2θ-angles given.

TABLE 1

Characteristic X-Ray powder diffractograms obtained using copper $K_{\alpha 1}$ radiation ($\lambda$ = 1.5406 Å) of the crystal forms alpha and beta of the hydrogen succinate salt of Compound I, and of the crystalline hydrogen malonate salt of Compound I. Fig; cf. also FIG. 1, FIG. 2 and FIG. 3 providing a representative XRPD pattern of polymorphic form alpha and beta of the hydrogen succinate salt and of the malonate salt of Compound I, respectively.

| Salt | Characteristic reflexes - main peaks (expressed in degree of diffraction angle 2θ) |
|---|---|
| Succinate, alpha | 9.36; 10.23; 11.81; 13.45; 16.21; 16.57; 17.49; 18.89; 19.20; 19.63; 20.01; 20.30; 21.15; 21.53; 21.93; 22.34; 24.37; 25.34; 27.27; 29.65 |
| Succinate, beta | 8.1; 10.5; 11.4; 14.0; 14.6; 15.6; 15.7; 16.2; 17.2; 17.5; 17.9; 18.4; 18.9; 19.2; 20.3; 21.0; 21.9; 22.5; 23.3; 26.3 |
| Malonatet | 8.3; 10.6; 11.5; 12.8; 14.2; 14.5; 14.7; 15.8; 16.5; 17.4; 17.6; 18.0; 18.6; 19.2; 21.2; 22.0; 22.9; 23.7; 24.7; 28.8 |

As used herein by expressions like "crystalline form of a specific salt of Compound I characterized by the X-Ray powder diffractogram shown in FIG. (1)" is meant the crystalline form of salt of Compound I in question having an X-ray powder diffractogram substantially similar to FIG. (1), i.e. exhibiting an X-ray powder diffraction pattern substantially as exemplified in that Figure and measured under comparable conditions as described herein or by any comparable method.

Generally, all data herein are understood to be approximate and subject to normal measurement error depending e.g. on the apparatus used and other parameters influencing peak positions and peak intensities.

The invention also relates to a solid hydrogen succinate salt of Compound I which solid salt consist mainly of the alpha form as compared to the total amount of the salt. In one embodiment, the term "mainly" means that the solid hydrogen succinate salt of Compound I consist of at least 75%, such as at least 80%, at least 90%, or at least 95% crystalline alpha form as compared to the total hydrogen succinate salt of Compound I present.

The invention also relates to a solid hydrogen succinate salt of Compound I which solid salt consist mainly of the beta form as compared to the total amount of the salt. In one embodiment, the term "mainly" means that the solid hydrogen succinate salt of Compound I consist of at least 75%, such as at least 80%, at least 90%, or at least 95% crystalline beta form as compared to the total hydrogen succinate salt of Compound I present.

The invention also relates to any mixtures of the crystalline forms of the hydrogen succinate salt of the invention, e.g. a mixture of the alpha and beta crystalline form of the hydrogen succinate salt of Compound I.

Preparation of the Salts of the Invention

The succinate salt according to the invention may be obtained by treatment of the free base of a compound of formula (I) with succinic acid in an inert solvent followed by precipitation, isolation and optionally recrystallization. If desired, the crystalline salt may thereafter be subjected to micronisation by wet or dry milling or another convenient process, or preparation of particles from a solvent-emulsification process.

Precipitation of the succinate salt of the invention is preferably carried out by dissolving the free base of the compound of formula (I) in a suitable solvent, such as acetone or toluene, and thereafter mixing this solution to a suspension or solution of succinic acid in a suitable solvent, such as acetone, aqueous acetone or toluene. In one embodiment the solvent is a mixture of acetone and water, e.g. a mixture consisting essentially of acetone and about 2% to 10%, preferably about 5% water, based on the weight of the mixture. The resulting suspension may be heated or solvent may be added until all succinic acid has dissolved. The succinate salt of the compound of the invention is precipitated, preferably upon cooling of the solution. The succinate salt of the invention may optionally be recrystallised one or more times and isolated by filtration, washed, e.g. with acetone, and dried.

The invention also relates to a method for the preparation of the crystalline beta form of the hydrogen succinate salt of Compound I, which method comprises leaving an aqueous solution of hydrogen succinate salt of Compound I for slow evaporation of the solvent at ambient conditions.

The malonate salt may be obtained using analogous procedures. Accordingly, the malonate salt according to the invention may be obtained by treatment of the free base of a compound of formula (I) with malonic acid in an inert solvent followed by precipitation, isolation and optionally recrystallisation. If desired, the crystalline salt may thereafter be subjected to micronisation by wet or dry milling or another convenient process, or preparation of particles from a solvent-emulsification process.

Precipitation of malonate salt of the invention is preferably carried out by dissolving the free base of the compound of formula (I) in a suitable solvent, e.g. 2-propanol, and thereafter mixing this solution to a suspension or solution of malonic acid in a suitable solvent, e.g. 2-propanol. The suspension may be heated until all malonic acid has dissolved. The malonate salt of the compound of the invention precipitated, preferably upon cooling of the solution. The malonate salt of the invention may optionally be recrystallised one or more times and isolated by filtration, washed, e.g. in 2-propanol, and dried.

Preparation of the Compound of Formula (I)

The compound of formula (I) in racemic form may be prepared as described in EP 638 073, and in Bøgesø et al. J. Med. Chem., 1995, 38, page 4380-4392, it is described how optical resolution of the racemic compound may be accomplished by crystallisation of diastereomeric salts thereby obtaining the enantiomer of formula (I).

The present inventors have now developed an improved route of synthesis in which the enantiomer of formula (I) is obtained via a synthetic sequence starting from enantiomeric pure V, i.e. compound Va((1S,3S)-6-chloro-3-phenylindan-1-ol, see below). Thus, in this process, the intermediate of formula V is resolved, e.g. by chiral chromatography or enzymatically, to obtain the enantiomer of formula Va. This new route of synthesis to obtain the compound of formula (I) is much more efficient than the above mentioned crystallisation of diastereomeric salts of the final product I. In particular the yield of the resolution is substantially higher in this new method (45% relative to the amount of racemic starting material, i.e. maximum theoretical yield is 50%) as compared to the yield (22% relative to the amount of racemic starting material, i.e. maximum theoretical yield is 50%) for the resolution of the final product I by crystallisation of diastereomeric salts. Another advantage of this invention is that the enantiomeric purity of (I) is higher (higher than 99%ee) when synthesised according to the invention as compared to the synthesis using crystallisation of diastereomeric salts (95.4%ee). Furthermore, the resolution of an intermediate instead of the final product gives a much more efficient synthesis, as only the right enantiomer is used in the subsequent steps, giving e.g. higher volume yields and less consumption of reagents.

Accordingly, the enantiomer of formula (I) may be obtained by a process involving the following steps:

Benzyl cyanide is reacted with 2,5-dichlorobenzonitril in the presence of a base, suitably potassium tert-butoxide (t-BuOK) in a suitable solvent such as dimethyl ether (DME), further reaction with methyl chloro acetate (MCA) leads to spontaneous ring closure and one pot formation of the compound of formula (II).

The compound of formula (II) is then subjected to acidic hydrolysis to form a compound of formula (III), suitably by heating in a mixture of acetic acid, sulphuric acid and water, and thereafter decarboxylation by heating the compound of formula (III) in a suitable solvent, such as toluene with triethyl amine or N-methyl pyrrolidone, to form a compound of formula (IV).

The compound of formula (IV) is then reduced, suitably with NaBH₄ in a solvent such as an alcohol, e.g. ethanol or iso-propanol, and preferably at a temperature in the range of −30° to +30° C., e.g. below 30° C., below 20° C., below 10° C., or preferably below 5° C., to form a compound of formula (V) with cis configuration:

The compound of formula (V) is resolved to achieve the desired enantiomer (formula Va), i.e. also with cis configuration ((1S,3S)-6-chloro-3-phenylindan-1-ol):

The resolution of (V) to (Va) may, e.g., be performed using chiral chromatography, preferably liquid chromatography, suitably on a chiral column of silicagel coated with a chiral polymer, e.g. a modified amylose, preferably amylose tris-(3, 5-dimethylphenylcarbamate) coated on silicagel. A suitable solvent is used for the chiral liquid chromatography, such as, e.g. an alcohol, a nitrile, an ether, or an alkane, or mixtures thereof, suitably ethanol, methanol, iso-propanol, acetonitrile, or methyl tert-butyl ether or mixtures thereof, preferably methanol or acetonitrile. The chiral liquid chromatography can be scaled up using suitable technologies, e.g. simulated moving bead technology (SMB).

Alternatively, the compound of formula (V) is resolved to achieve Compound Va by enzymatic resolution. It has been found that enantiomerically pure Compound Va, or acylated derivatives thereof, may be prepared by enzymatic enantioselective acylation of the hydroxyl group in racemic Compound V to obtain Compound Va or an acylated derivative thereof with high optical purity. Alternatively, enantiomerically pure Compound Va may also be obtained by a process comprising converting racemic Compound V to a corresponding ester in the hydroxyl position followed by an enzymatic enantioselective deacylation. Use of enzymatic enantioselective deacylation has been reported for other compounds.

Accordingly, The resolution of Compound V to Compound Va may be performed by selective enzymatic acylation. Selective enzymatic acylation means that the enzymatic acylation is preferentially effective for conversion of one of the cis-enantiomers of the compound of formula Compound V leaving the other cis-enantiomer of Compound V as unconverted in the reaction mixture.

Alternatively, The resolution of Compound V to Compound Va may be performed by selective enzymatic deacylation. Selective enzymatic deacylation means that the enzymatic deacylation is preferentially effective for conversion of one of the esters of compound of formula (V), leaving the other cis-enantiomer of esters of a compound of formula (V) as unconverted in the reaction mixture.

Suitable esters (Vb) of the compound of formula (V) are ester such as acetate, propionate, butyrate, valerate, hexanoate, benzoate, laurate, isobutyrate, 2-methylbutyrate, 3-methylbutyrate, pivalate, 2-methylvalerate, 3-methylvalerate, 4-methylvalerate wherein R, e.g., is acetate, propionate, butyrate, valerate, hexanoate, benzoate, laurate, isobutyrate, 2-methylbutyrate, 3-methylbutyrate, pivalate, 2-methylvalerate, 3-methylvalerate, 4-methylvalerate.

Thus, one embodiment relates to a process for the preparation of the (S, S)- or (R, R)-enantiomer of the compound of formula V (i.e. with cis configuration) comprising:
a) subjecting a racemic Compound V to enantioselective enzymatic acylation using an acylating agent, or
b) subjecting a racemic Compound Vb to entantioselective enzymatic deacylation to form a mixture of deacylated Compound Va.

Enantioselective enzymatic acylation means that the enzymatic acylation is preferentially effective for conversion of one of the enantiomers of a compound of formula (V) preferentially leaving the other enantiomer of the compound of formula (V) unconverted in the reaction mixture. Enantioselective enzymatic deacylation means that the enzymatic deacylation is preferentially effective for conversion of one of the enantiomers of a compound of formula (Vb), preferentially leaving the other enantiomer of the compound of formula (Vb) unconverted in the reaction mixture.

The mixtures obtained by the enzymatic resolution may not be entirely pure, e.g. they may contain a smaller amount of the other enantiomer in addition to a larger amount of the desired enantiomer (Va). The composition mixture obtained after acylation or deacylation according to the invention depend, i.a., on the specific hydrolase used and the conditions under which the reaction is carried out. Characteristic of the enzymatic acylation/deacylation according to the invention is that a considerably larger portion of one enantiomer is converted than of the other. The enantioselective acylation according to the invention thus results in a mixture containing preferentially the compound of formula (Vb) in the (R, R-form and the compound of formula (Va) in the (S, S)-form, or it may result in a mixture containing preferentially the compound of formula (Vb) in the (S, S)-form and the compound of formula (Va) in the (R, R)-form. Likewise, the enantioselective enzymatic deacylation may result in a mixture containing preferentially the compound of formula (Vb) in the (S, S)-form and the compound of formula (V) in the (R, R)-form, or it may result in a mixture containing preferentially the compound of formula (Va) in the (R, R)-form and the compound of formula (Va) in the (S, S)-form. The optical purity of the Va obtained by the optical resolution method of the present invention is usually at least 90% ee., preferably at least 95% ee., more preferably at least 97% ee and most preferably at least 98% ee. However, lower values for the optical purity are acceptable.

According to the invention, enantioselective enzymatic acylation is carried out under conditions substantially suppressing hydrolysis. Hydrolysis, which is the reverse reaction of the acylation reaction, takes place if water is present in the reaction system. Thus, enantioselective enzymatic acylation is preferably carried out in a water-free organic solvent or almost anhydrous organic solvent (enzymes normally require the presence of some water to be active). Suitable solvents include hydrocarbons such as hexane, heptane, benzene and toluene; ethers such as diethyl ether, diisopropyl ether, tetrahydrofuran, 1,4-dioxane, tert-butyl methyl ether and dimethoxyethane; ketones such as acetone, diethyl ketone, butanon, and methyl ethyl ketone; esters such as methyl acetate, ethyl acetate, ethyl butyrate, vinyl butyrate and ethyl benzoate; halogenated hydrocarbons such as methylene chloride, chloroform and 1,1,1-trichloroethane; secondary and tertiary alcohols, such as tert-butanol; nitrogen-containing solvents such as dimethylformamide, acetoamide, formamide, acetonitrile and propionitrile; and aprotic polar solvents such as dimethylsulfoxide, N-methylpyrrolidone and hexamethylphosphorous triamide. Preferred organic solvents for enzymatic acylation are organic solvents such as toluene, hexane, heptane, dioxane and tetrahydrofuran (THF).

Suitable irreversible acyldonors are, e.g., acyldonors such as vinyl-esters, 2-propenyl-esters or 2,2,2-trihalid-ethyl-esters.

Enantioselective enzymatic deacylation is preferably carried out in water or a mixture of water and an organic solvent, suitable in presence of a buffer. Suitable organic solvents, e.g., are solvents miscible with water such as alcohols, acetonitrile, dimethyl formamide (DMF), dimethyl sulfoxide (DMSO), 1,4-dioxane, DME and diglyme.

It has been found that enzymatic acylation according to the invention may be carried out using Novozym 435 (Candida Antarctica lipase B, from Novozymes A/S, Fluka Cat.-No. 73940). In general, the enzymatic acylation or deacylation according to the invention is preferably carried out using a lipase, an esterase, an acylase or a protease. The enzymes useful according to the invention are such enzymes capable of performing R-selective acylation or S-selective acylation of the hydroxy group in the racemic compound of formula (V) or such enzymes which are capable of performing R-selective deacylation or S-selective deacylation of the acyl group in the racemic compound of formula (Vb). In particular immobilized forms of the enzyme, including Cross-Linked Enzyme Crystal (CLEC) are useful according to the invention. A preferred embodiment relates to use of a lipase for carrying out the enzymatic resolution of Compound V. The most preferred lipase is Candida antarctica lipase (Fluka Cat.-No. 62299); Pseudomonas cepacia lipase (Fluka Cat.-No. 62309); Novozym CALB L (Candida antarctica lipase B) (Novozymes A/S); Novozym 435 (Candida antarctica lipase B)

(Novozymes A/S); or Lipozyme TL IM (Thermomyces lanuginosus lipase) (Novozymes A/S), preferably in immobilized form.

The alcohol group of the cis-alcohol of formula (Va) is converted to a suitable leaving group, such as, e.g., a halogen, e.g. Cl or Br, preferably Cl, or a sulphonate, e.g. mesylate or tosylate, suitably by reaction with an agent, such as thionyl chloride, mesyl chloride or tosyl chloride, in an inert solvent, e.g. an ether, suitably tetrahydrofuran. The resulting compound has formula (VI), where LG is the leaving group:

(VI)

In a preferred embodiment, LG is Cl, i.e. the cis-chloride of formula (VIa):

(VIa)

Compound VI, e.g. with LG as chloro, is then reacted with 2,2-dimethylpiperazine in a suitable solvent, e.g. a ketone such as, e.g., methyl isobutyl ketone or methyl ethyl ketone, preferably methyl isobutyl ketone in presence of a base, such as e.g., potassium carbonate. The resulting compound of formula (VII):

(VII)

is methylated at the secondary amine functionality (suitably by reductive amination using suitable agents, such as, e.g., formaldehyde, paraformaldehyde, trioxane, or diethoxy methane (DEM) to obtain the free base of a compound of formula (I).

(I)

Alternatively, the methyl group may be introduced directly by use of 1,2,2-trimethyl piperazine (Formula VIII below) instead of 2,2-dimethyl piperazine when reacting with Compound VI, e.g. where LG is Cl, thereby shortening the synthesis by one step.

(VIII)

Furthermore, the piperazine part of the molecule may be introduced by reacting Compound VI with a compound of formula (IX) below, where PG is a protecting group such as, but not restricted to, e.g. phenylmethoxycarbonyl (often called Cbz or Z), tert-butyloxycarbonyl (often called BOC), ethoxycarbonyl, or benzyl, thereby obtaining the compound of formula (X) below.

(IX)

(X)

After deprotection of the product to (VII), methylation as discussed above gives the final product, Compound I. Alternatively, the protecting group such as e.g. ethoxycarbonyl may be converted directly to a methyl group using a suitable reducing agent, e.g. lithium aluminium hydride.

During the synthesis some cis diastereoisomer of Compound I (i.e. 4((1S,3S)-6-chloro-3-phenylindan-1-yl)-1,2,2-trimethylpiperazine) is formed as an impurity in the final product. This impurity is due mainly to the formation of some of the traits form of (VI) (e.g. (1S,3R)-3,5-dichloro-1-phenylindan when LG is Cl) in the step where Compound VI is formed. Therefore, the impurity can be minimized by crystallisation of the desired cis form of Compound VI, from the mixture of trans and cis (VI); in the case where LG is Cl in Compound VI this can be done by stirring the mixture with a suitable solvent, e.g. an alkane, such as heptane, whereby the desired cis form of VI precipitates and the undesired trans form of Compound VI goes into solution. The desired cis form of Compound VI (e.g. when LG is Cl) is isolated by filtration, washed with the solvent in question and dried.

If the cis form of Compound VI is present in the batch of (VI) used in the synthesis of Compound VII, this will give raise to the formation of the trans form of Compound VII (i.e. 4-((1S,3S)-6-chloro-3-phenylindan-1-yl)-3,3-dimethylpiperazine) as an impurity in (VII); this gives a second option of avoiding the cis form of Compound I in the final product: It has been found that the cis form of Compound VII can be removed by precipitation of a suitable salt of the compound of formula Compound VII, e.g. a salt of an organic acid, such as an organic diacid, suitably the hydrogen fumarate salt or the hydrogen maleate salt of the compound of formula (VII), optionally followed by one more re-crystallisations.

Furthermore, it has been found that impurities in the form of cis diastereoisomer in (I) (i.e. 4-((1S,3S)-6-chloro-3-phenylindan-1-yl)-1,2,2-trimethylpiperazine) may effectively be removed by precipitation of a suitable salt of the compound of formula (I), e.g. a salt of an organic acid, such as an organic diacid, suitably a fumarate salt, e.g. the hydrogen fumarate salt of the compound of formula (I) optionally followed by one or more re-crystallisations.

The invention in further aspects also relates to the intermediates as described herein for the synthesis of the compound of formula (I), i.e. in particular the intermediates (Va), VI, e.g. VIa, and VII, or salts of Compound VII. In this context is understood that when specifying the stereoisomeric form, then the stereoisomer is the main constituent of the compound. In particular, when specifying the enantiomeric form, then the compound has an enantiomeric excess of the enantiomer in question.

Accordingly, one embodiment of the invention relates to the compound of formula (Va), preferably having an enantiomeric excess of at least 60% (60% enantiomeric excess means that the ratio of Va to its enantiomer is 80:20 in the mixture in question), at least 70%, at least 80%, at least 85%, at least 90%, at least 96%, preferably at least 98%. Furthermore, the diastereomeric excess of the compound is preferably at least 70% (70% diastereomeric excess means, that the ratio of Compound Va to (1R,3S)-6-chloro-3-phenylindan-1-ol is 85:15 in the mixture in question), at least 80%, at least 85%, at least 90%, or at least 95%. One embodiment relates to substantially pure Compound Va.

A further embodiment of the invention relates to the compound of formula (VI), preferably having an enantiomeric excess of at least 60%, at least 70%, at least 80%, at least 85%, at least 90%, at least 96%, preferably at least 98%, (VI)

wherein LG is a potential leaving group, preferably selected from the group consisting of a halogen, e.g. chloride, or a sulphonate. One embodiment relates to the diastereomeric purity of Compound VI; i.e. the compound having a diastereomeric excess of preferably at least 10% (10% diastereomeric excess means that the ratio of Compound VI to the cis diastereoisomer (e.g. (1S,3R)-3,5-dichloro-1-phenylindan when LG=Cl) is 55:45 in the mixture in question), at least 25% or at least 50%. One embodiment, relates to substantially pure Compound VI.

Accordingly, the invention also relates to a compound having the following formula (VIa), (VIa)

preferably having an enantiomeric excess of at least 60%, at least 70%, at least 80%, at least 85%, at least 90%, at least 96%, preferably at least 98%. One embodiment relates to the diastereomeric purity of the compound, i.e. the compound having a diastereomeric excess of, preferably at least 10% (10% diastereomeric excess means that the ratio of the compound to the cis diastereoisomer, (1S,3R)-3,5-dichloro-1-phenylindan, is 55:45 in the mixture in question), at least 25% or at least 50%. One embodiment relates to substantially pure Compound VI where LG is Cl.

The invention also relates to a compound (VII) having the structure:

(VII)

preferably having an enantiomeric excess of at least 60% (60% enantiomeric excess means that the ratio of VII to its enantiomer is 80:20 in the mixture in question), at least 70%, at least 80%, at least 85%, at least 90%, at least 96%, preferably at least 98%, or a salt thereof, such as, e.g., a fumarate salt, e.g. hydrogen fumarate, or a maleate salt, e.g. hydrogen maleate. One embodiment relates to the diastereomeric purity of the Compound VII, i.e. the compound having a diastereomeric excess of preferably at least 10% (10% diastereomeric excess means that the ratio of Compound VII to the cis-(1S, 3S) diastereoisomer is 55:45 in the mixture in question), at least 25%, at least 50%, at least 70%, at least 80%, at least 90%, at least 95%, at least 97%, at least 98%. One embodiment relates to substantially pure Compound VII or a salt thereof.

A further aspect relates to Compound I or a salt thereof, in particular the fumarate, malonate, or succinate salt, obtainable, in particular obtained, by a method of the invention as described herein.

A further aspect relates to Compound VII or a salt thereof, e.g. the fumarate salt, obtainable, in particular obtained, by a method of the invention as described herein.

Pharmaceutical Use

The physical properties of the Compound I salts of the invention indicate that they will be particularly useful as a pharmaceutical.

Accordingly, the present invention further relates to a pharmaceutical composition of the succinate salt, in particular the hydrogen succinate salt as described herein (e.g. the alpha or beta form as described herein), or of the malonate salt, in particular the hydrogen malonate salt, of the compound of formula (I). The invention also relates to the medical use of such salts and compositions, such as for the treatment of a disease in the central nervous system, including psychosis, in particular schizophrenia or other diseases involving psychotic symptoms, such as, e.g., Schizophrenia, Schizophreniform Disorder, Schizoaffective Disorder, Delusional Disorder, Brief Psychotic Disorder, Shared Psychotic Disorder as well other psychotic disorders or diseases that present with psychotic symptoms, e.g. mania in bipolar disorder.

Additionally, the 5-$HT_2$ antagonistic activity of compound of the invention suggests that the compound may have a relatively low risk of extrapyramidal side effects.

The present invention also relates to use of the succinate or malonate salt of the invention, preferably the hydrogen succinate (e.g. the crystalline form alpha) or hydrogen malonate salt, of the compound of formula (I) for treatment of a disease selected from the group consisting of anxiety disorders, affective disorders including depression, sleep disturbances, migraine, neuroleptic-induced parkinsonism, cocaine abuse, nicotine abuse, alcohol abuse and other abuse disorders.

In a broad aspect, the present invention relates to a method of treating Schizophreniform Disorder, Schizoaffective Disorder, Delusional Disorder, Brief Psychotic Disorder, Shared Psychotic Disorder or mania in bipolar disorder, comprising administering a therapeutically effective amount of the compound trans-4-(6-chloro-3-phenylindan-1-yl)-1,2,2-trimethylpiperazine or a salt thereof.

As used herein the term "trans-4-(6-chloro-3-phenylindan-1-yl)-1,2,2-trimethylpiperazine", i.e. without any specific indication of the enantiomer form (e.g. using (+) and (−), or using the R/S-convention, is meant to refer to any enantiomeric form of this compound, i.e. either of the two enantiomers, 4-((1R,3S)-6-chloro-3-phenylindan-1-yl)-1,2,2-trimethylpiperazine (I) or 4-((1S,3R)-6-chloro-3-phenylindan-1-yl)-1,2,2-trimethylpiperazine or to a mixture of the two, e.g. the racemic mixture. However, in this context preferably the content of the enantiomer corresponding to that of Compound I is at least 50%, i.e. at least as the racemic mixture, preferably Compound I is in enantiomeric excess.

In the present context for the pharmaceutical uses it is understood that when specifying the enantiomer form of the compound trans-4-(6-chloro-3-phenylindan-1-yl)-1,2,2-trimethylpiperazine (e.g. as done in formula (I)), then the compound is relatively stereochemically pure as described above, preferably the enantiomeric excess is of at least 80% (80% enantiomeric excess means that the ratio of I to its enantiomer is 90:10 in the mixture in question) at least 90%, at least 96%, or preferably at least 98%. In a preferred embodiment, the diastereomeric excess of Compound I is at least 90% (90% diastereomeric purity means the ratio of Compound I to cis-4-((1S,3S))-6-chloro-3-phenylindan-1-yl)-1,2,2-trimethylpiperazine is 95:5), at least 95%, at least 97%, or at least 98%.

In a preferred embodiment, the present invention relates to a method of treating Schizophreniform Disorder, Schizoaffective Disorder, Delusional Disorder, Brief Psychotic Disorder, Shared Psychotic Disorder or mania in bipolar disorder, comprising administering a therapeutically effective amount of the compound of formula (I) [i.e. 4-((1R,3S)-6-chloro-3-phenylindan-1-yl)-1,2,2-trimethylpiperazine] or a salt thereof.

One embodiment of the invention relates to a method of treating positive symptoms of schizophrenia, negative symptoms and depressive symptoms of schizophrenia comprising administering a therapeutically effective amount of the compound trans-4-(6-chloro-3-phenylindan-1-yl)-1,2,2-trimethylpiperazine or a salt thereof, preferably the compound of formula (I) or a salt thereof, or in a preferred embodiment a succinate or a malonate salt of the compound of formula (I), preferably the hydrogen succinate or the hydrogen malonate salt of the compound of formula (I).

A further embodiment of the invention relates to a method of treating positive symptoms of schizophrenia comprising administering a therapeutically effective amount of the compound trans-4-(6-chloro-3-phenylindan-1-yl)-1,2,2-trimethylpiperazine or a salt thereof, preferably the compound of formula (I) or a salt thereof, or in a preferred embodiment a succinate or a malonate salt of the compound of formula (I), preferably the hydrogen succinate or the hydrogen malonate salt of the compound of formula (I).

Another embodiment of the invention relates to a method of treating negative symptoms of schizophrenia comprising administering a therapeutically effective amount of the compound trans-4-(6-chloro-3-phenylindan-1-yl)-1,2,2-trimethylpiperazine or a salt thereof, or preferably the compound of formula (I) or a salt thereof, or in a preferred embodiment a succinate or a malonate salt of the compound of formula (I), preferably the hydrogen succinate or the hydrogen malonate salt of the compound of formula (I).

A further embodiment of the invention relates to a method of treating depressive symptoms of schizophrenia comprising administering a therapeutically effective amount of the compound trans-4-(6-chloro-3-phenylindan-1-yl)-1,2,2-trimethylpiperazine or a salt thereof, preferably the compound of formula (I) or a salt thereof, or in a preferred embodiment the hydrogen succinate or malonate salt of the compound of formula (I).

A further aspect of the invention relates to a method of treating mania and/or maintenance of bipolar disorder comprising administering a therapeutically effective amount of the compound trans-4-(6-chloro-3-phenylindan-1-yl)-1,2,2-trimethylpiperazine or a salt thereof, preferably the compound of formula (I) or a salt thereof, or in a preferred embodiment a succinate or a malonate salt of the compound of formula (I), preferably the hydrogen succinate or the hydrogen malonate salt of the compound of formula (I).

A further aspect of the invention relates to a method of treating neuroleptic-induced parkinsonism comprising administering a therapeutically effective amount of the compound trans-4-(6-chloro-3-phenylindan-1-yl)-1,2,2-trimethylpiperazine or a salt thereof, preferably the compound of formula (I) or a salt thereof, or in a preferred embodiment a succinate or a malonate salt of the compound of formula (I), preferably the hydrogen succinate or the hydrogen malonate salt of the compound of formula (I).

The invention further relates to a method of treating substance abuse, e.g. nicotine, alcohol or cocaine abuse, comprising administering a therapeutically effective amount of the compound trans-4-(6-chloro-3-phenylindan-1-yl)-1,2,2-trimethylpiperazine or a salt thereof, preferably the compound of formula (I) or a salt thereof, or in a preferred embodiment a succinate or a malonate salt of the compound of formula (I), preferably the hydrogen succinate or the hydrogen malonate salt of the compound of formula (I).

A salt or a composition of the invention may be administered in any suitable way e.g. orally, buccal, sublingual or parenterally, and the salt may be presented in any suitable form for such administration, e.g. in the form of tablets, capsules, powders, syrups or solutions or dispersions for injection. In one embodiment, a salt of the invention are administered in the form of a solid pharmaceutical entity, suitably as a tablet or a capsule.

Methods for the preparation of solid pharmaceutical preparations are well known in the art. Tablets may thus be prepared by mixing the active ingredient with ordinary adjuvants, fillers and diluents and subsequently compressing the mixture in a convenient tabletting machine. Examples of adjuvants, fillers and diluents comprise corn starch, lactose, talcum, magnesium stearate, gelatine, lactose, gums, and the like. Any other adjuvant or additive such as colourings, aroma, preservatives, etc. may also be used provided that they are compatible with the active ingredients. Solutions for injections may be prepared by dissolving a salt of the invention and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, solubilising agents etc.

The daily dose of the compound of formula (I) above, calculated as the free base, is suitably between 1.0 and 160 mg/day, more suitable between 1 and 100 mg, e.g. preferably between 2 and 55, or between 3 and 55 mg.

The term "treatment" as used herein in connection with a disease or disorders includes also prevention as the case may be.

The invention will be illustrated in the following non-limiting examples.

EXAMPLES

Compound Preparation

Analysis

The enantiomeric excess of compound (Va) in Example 1a is determined by chiral HPLC using a CHIRALCEL® OD column, 0.46 cm ID×25 cm L, 10 µm at 40° C. n-Hexan/ethanol 95:5 (vol/vol) is used as mobile phase at a flow rate of 1.0 ml/min, detection is performed using a UV detector at 220 nm.

HPLC analysis for conversion rate used for Examples 1b:

Column: A Lichrospher RP-8 column, 250×4 mm (5 µm particle size) Eluent: Buffered MeOH/water prepared as follows: 1.1 ml Et$_3$N added to 150 ml water, 10% H$_3$PO$_4$(aq) is added to pH=7 and water is added to a total of 200 ml. The mixture is added to 1.8 L MeOH.

The enantiomeric excess of compound (Va) in example 1b is determined by chiral HPLC using a CHIRALPAK® AD column, 0.46 cm ID×25 cm L, 10 µm at 21° C. Heptane/ethanol/Diethylamine 89.9:10:0.1 (vol/vol/vol) is used as mobile phase at a flow rate of 1.0 ml/min, detection is performed using a UV detector at 220 nm.

The enantiomeric excess of Compound I is determined by fused silica capillary electrophoresis (CE) using the following conditions: Capillar: 50 µm ID×64.5 cm L, run buffer: 1.25 mM β cyclo dextrin in 25 mM sodium dihydrogen phosphate, pH 1.5, voltage: 16 kV, temperature: 22° C., injection: 50 mbar for 5 seconds, detection: column diode array detection 192 nm, sample concentration: 500 µg/ml. In this system, Compound I has a retention time of approximately 33 min, and the other enantiomer has a retention time of approximately 35 min.

$^1$H NMR spectra are recorded at 500.13 MHz on a Bruker Avance DRX500 instrument or at 250.13 MHz on a Bruker AC 250 instrument. Chloroform (99.8%D) or dimethyl sulfoxide (99.8%D) is used as solvents, and tetramethylsilane (TMS) is used as internal reference standard.

The cis/trans ratio of compounds I and VII is determined using $^1$H NMR as described in Bøgesø et al., *J. Med. Chem.* 1995, 38, 4380-4392 (page 4388, right column). The cis/trans ratio of compound VI is also determined by $^1$H NMR in chloroform, using the integrals of the signal at 5.3 ppm for the cis isomer and the signal at 5.5 ppm for the trails isomer. Generally, a content of approximately 1% of the undesired isomer can be detected by NMR.

X-Ray powder diffractograms are recorded at a PANalytical X'Pert PRO X-Ray Diffractometer using CuK$_{\alpha 1}$ radiation. It is measured in reflection mode in the 2θ-range 5-40°.

The Melting points are measured using Differential Scanning Calorimetry (DSC). The equipment is a TA-Instruments DSC-2920 calibrated at 5°/min to give the melting point as onset value. About 2 mg of sample is heated 5°/min in a loosely closed pan under nitrogen flow.

Synthesis of Key Starting Material

Compound V was synthesised from IV by reduction with sodium borohydride (NaBH$_4$) adapting a method described in Bøgesø *J Med. Chem.* 1983, 26, 935, using ethanol as solvent, and performing the reaction at approximately 0° C. Both compounds are described in Bøgesø et al. *J Med. Chem.* 1995, 38, 4380-4392. Compound IV was synthesised from II using the general procedures described in Sommer et al., *J. Org. Chem.* 1990, 55, 4822, which also describes II and the synthesis thereof.

Example 1a

Synthesis of (1S,3S)-6-chloro-3-phenylindan-1-ol (Va) by Use of Chiral Chromatography Racemic cis-6-chloro-3-phenylindan-1-ol (V) (492 grams) is resolved by preparative chromatography, using a CHIRALPAK® AD column, 10 cm ID×50 cm L, 10 µm at 40° C. Methanol is used as mobile phase at a flow rate of 190 ml/min, detection is performed using a UV detector at 287 nm. The racemic alcohol (V) is injected as a 50,000 ppm solution in methanol; 90 ml is injected with intervals of 28 min. All the fractions, which contain the title compound with more than 98% enantiomeric excess, are combined and evaporated to dryness using a rotary evaporator, followed by drying "in vacuo" at 40° C. Yield 220 grams as a solid. Elemental analysis and NMR conform to the structure, the enantiomeric excess is higher than 98% according to chiral HPLC, $[\alpha]_D^{20}$+44.5° (c=1.0, methanol).

Example 1b

Synthesis of (1S,3S)-6-chloro-3-phenylindan-1-ol (Va) by Use of Enzymatic Esolution Compound V (5 g, 20.4 mmol) is dissolved in 150 ml anhydrous toluene. 0.5 g Novozym 435 (Candida Antarctica lipase B) (Novozymes A/S, Fluka Cat.-No. 73940) is added followed by vinylbutyrate (13 ml, 102.2 mmol). The mixture is stirred using mechanical stirrer at 21° C. After 1 day, an additional 0.5 g Novozym 435 is added. After 4 days at a conversion of 54%, the mixture is filtered and concentrated in vacuo to obtain an oil containing a mixture of (1R, 3R)-cis-6-chloro-3-phenylindan-1-ol-butyrate ester and desired compound Va with an enantiomeric excess of 99.2% (99.6% compound Va and 0.4% (1R, 3R)-cis-6-chloro-3-phenylindan-1-ol).

Synthesis of (I) and Removal of the Impurity in form of the cis Diastereoisomer by Precipitation of the Hydrogen Fumarate Salt of (I)

Example 2

Synthesis of (1S,3S)-3,5-dichloro-1-phenylindan (VI, LG=Cl)

Cis-(1S,3S)-6-chloro-3-phenylindan-1-ol (Va) (204 grams) obtained as described in Example 1a is dissolved in THF (1500 ml) and cooled to −5° C. Thionyl chloride (119 grams) is added dropwise as a solution in THF (500 ml) over a period of 1 h. The mixture is stirred at room temperature over night. Ice (100 g) is added to the reaction mixture. When the ice has melted the water phase (A) and the organic phase (B) are separated, and the organic phase B is washed twice with saturated sodium bicarbonate (200 ml). The sodium bicarbonate phases are combined with water phase A, adjusted to pH 9 with sodium hydroxide (28%), and used to wash the organic phase B once again. The resulting water phase (C) and the organic phase B are separated, and the water phase C is extracted with ethyl acetate. The ethyl acetate phase is combined with the organic phase B, dried with magnesium sulphate, and evaporated to dryness using a rotary evaporator, giving the title compound as an oil. Yield 240 grams, which is used directly in the example 5. Cis/trans ratio 77:23 according to NMR.

Example 3

Synthesis of 3,3-dimethylpiperazin-2-one

Potassium carbonate (390 grams) and ethylene diamine (1001 grams) are stirred with toluene (1.50l). A solution of ethyl 2-bromoisobutyrate (500 grams) in toluene (750 ml) is added. The suspension is heated to reflux over night, and filtered. The filter cake is washed with toluene (500 ml). The combined filtrates (volume 4.0l) are heated on a water bath and distilled at 0.3 atm. using a Claisen apparatus; first 1200 ml distillate is collected at 35° C. (the temperature in the mixture is 75° C.). More toluene is added (600 ml), and another 1200 ml distillate is collected at 76° C. (the temperature in the mixture is 80° C.). Toluene (750 ml) is added again, and 1100 ml of distillate is collected at 66° C. (temperature in the mixture 71° C.). The mixture is stirred on an ice bath and inoculated, whereby the product precipitates. The product is isolated by filtration, washed with toluene, and dried over night in a vacuum oven at 50° C. Yield 171 g (52%) of 3,3-dimethylpiperazin-2-one. NMR consistent with structure.

Example 4

Synthesis of 2,2-dimethylpiperazine

A mixture of 3,3-dimethylpiperazin-2-one (8.28 kg, 64.6 mol) and tetrahydrofuran (THF) (60 kg) is heated to 50-60° C. giving a slightly unclear solution. THF (50 kg) is stirred under nitrogen, and LiAlH$_4$ (250 g, in a soluble plastic bag, from Chemetall) is added, which gives a slow evolution of gas. After gas evolution has ceased, more LiAlH$_4$ is added (a total of 3.0 kg, 79.1 mol, is used), and the temperature rises from 22° C. to 50° C. because of an exoterm. The solution of 3,3-dimethylpiperazin-2-one is added slowly over 2 hours at 41-59° C. The suspension is stirred for another hour at 59° C. (jacket temperature 60° C.). The mixture is cooled, and water (3l) is added over two hours, keeping the temperature below 25° C. (it is necessary to cool with a jacket temperature of 0° C.). Then sodium hydroxide (15%, 3.50 kg) is added over 20 minutes at 23° C., cooling necessary. More water (9l) is added over half an hour (cooling necessary), and the mixture is stirred over night under nitrogen. Filter agent Celit (4 kg) is added, and the mixture is filtered. The filter cake is washed with THF (40 kg). The combined filtrates are concentrated in the reactor until the temperature in the reactor is 70° C. (distillation temperature 66° C.) at 800 mbar. The remanence (12.8 kg) is further concentrated on a rotavapor to approximately 10l. Finally, the mixture is fractionally distilled at atmospheric pressure, and the product is collected at 163-4° C. Yield 5.3 kg (72%). NMR complies with the structure.

Example 5

Synthesis of trans-1-((1R,3S)-6-chloro-3-phenylindan-1-yl)-3,3-dimethylpiperazine (VII)

Cis-(1S,3S)-3,5-dichloro-1-phenylindan (VI, LG=Cl) (240 g) is dissolved in butan-2-one (1800 ml). Potassium carbonate (272 g) and 2,2-dimethyl piperazine (prepared in Example 4) (113 g) are added and the mixture is heated at reflux temperature for 40 h. To the reaction mixture is added diethyl ether (21) and hydrochloric acid (1M, 61). The phases are separated, and pH in the water phase is lowered from 8 to 1 with concentrated hydrochloric acid. The water phase is used to wash the organic phase once again in order to ensure, that all product is in the water phase. Sodium hydroxide (28%) is added to the water phase until pH is 10, and the water phase is extracted twice with diethyl ether (21). The diethyl ether extracts are combined, dried with sodium sulphate, and evaporated to dryness using a rotary evaporator. Yield 251 grams of the title compound as an oil, which is used directly in the next example. Cis/trans ratio, 82:18 according to NMR.

Example 6

Synthesis of trans-4-((1R,3S)-6-chloro-3-phenylindan-1-yl)-1,2,2-trimethylpiperazinium (I) Hydrogen Fumarate Crude trans-1-((1R,3S)-6-chloro-3-phenylindan-1-yl)-3,3-dimethylpiperazine (VII) (250 grams) is mixed with formaldehyde (37% in water, 300 ml) and formic acid (366 grams), and the mixture is slowly heated to reflux. The mixture is stirred at reflux for 3.5 hours, and after cooling to room temperature, water (1200 ml) is added. The mixture is extracted twice with ether (1200 ml), and then the water phase is made alkaline by adding sodium hydroxide (28%, approximately 500 ml). The water phase is extracted three times with ether (900 ml). The organic phases are combined and washed with brine (650 ml), and twice with water (500 ml). The organic phase is dried by sodium sulphate, filtered and evaporated to dryness on a rotary evaporator. Yield: 212 grams of trans-4-((1R,3S)-6-chloro-3-phenylindan-1-yl)-1,2,2-trimethylpiperazine free base (I) as an oil, with 19% of the cis diastereoisomer according to NMR. The compound is dissolved in 1-propanol (3.18 l) and the mixture is heated to 50° C., which gives a clear solution. Fumaric acid (69.3 grams) is added, giving a clear solution. The mixture is allowed to cool, whereby the title compound precipitates. The product is isolated by filtration, washed with 1-propanol, and dried "in vacuo" at 60° C.

Yield: 182 grams, contains <1% of the cis diastereoisomer according to NMR. Elemental analysis and NMR conform to the structure. The enantiomeric excess is higher than 99% according to chiral capillary electrophoreses (CE). $[\alpha]_D^{20}$=22.8° (c=1.0, methanol).

Liberation of the Free Amine of (I) from the Hydrogen Fumarate Salt and Reprecipitation as Hydrogen Succinate and Hydrogen Malonate Salts

Example 7

Synthesis of 4-((1R,3S)-6-chloro-3-phenylindan-1-yl)-1,2,2-trimethylpiperazine Free Base (I)

Trans-4-((1R,3S)-6-chloro-3-phenylindan-1-yl)-1,2,2-trimethylpiperazinium (I) hydrogen fumarate (25.0 grams) is suspended in toluene (125 ml). Aqueous ammonia 25% (75 ml) is added. The three phases are stirred until all solids have disappeared. The organic phase is separated, and the aqueous phase is washed with toluene (25 ml). The combined toluene phases are washed with water (25 ml). The aqueous phase is discarded and the organic phase is dried by sodium sulphate sicc. (35 grams), the slurry is filtered and the filtrate is evaporated to dryness on a rotary evaporator, giving the title compound as an oil. The crude free base (15 grams) is used without further purification.

Example 8

Synthesis of traits-4-((1R,3S)-6-chloro-3-phenylindan-1-yl)-1,2,2-trimethyl-piperazinium (I) Hydrogen Succinate Crude trans-4-((1R,3S)-6-chloro-3-phenylindan-1-yl)-1,2,2-trimethylpiperazine (I) (8.50 grams of oil) obtained as described in Example 7 is dissolved in acetone (30 ml). A suspension of succinic acid (3.25 grams) in acetone (32 ml) is prepared and the trans-4-((1R,3S)-6-chloro-3-phenylindan-1-yl)-1,2,2-trimethylpiperazine (I) solution is added, the succinic acid dissolves and shortly thereafter the trans-4-((1R,3S)-6-chloro-3-phenylindan-1-yl)-1,2,2-trimethylpiperazinium (I) hydrogen succinate precipitates. The suspension is cooled to 0° C. for 90 minutes before the precipitate is isolated by centrifugation. The supernatant is discarded and the precipitate is washed with acetone (20 ml). The slurry is centrifuged and the supernatant is discarded and the precipitate is dried "in vacuo" at 50° C.

Yield 8.56 grams.

When this procedure was performed for the first time the isolated product was the beta-form, following repetitions resulted in formation of the more stable alpha-form of Compound I hydrogen succinate.

Acetone in the above described experiment can be substituted by aqueous acetone (95%) also resulting I formation of the alpha-form of Compound I hydrogen succinate. Differential Scanning Calorimetry (DSC) shows an endotherm with an onset temperature of 140° C. and a peak at 141° C. corresponding to the alpha form. XRPD diffractogram conforms with the alpha form.

Example 9 trans-4-((1R,3S)-6-chloro-3-phenylindan-1-yl)-1,2,2-trimethylpiperazinium (I) Hydrogen Malonate Crude trans-4-((1R,3S)-6-chloro-3-phenylindan-1-yl)-1,2,2-trimethylpiperazine (I) (1.0 gram, 2.81 mmol, obtained as described in Example 7 is dissolved in 2-propanol (5 ml). A solution of malonic acid (0.291 grams, 2.46 mmol) in 2-propanol (5 ml) is prepared and the trans-4-((1R,3S)-6-chloro-3-phenylindan-1-yl)-1,2,2-trimethylpiperazine solution is added, whereby the trans-4-((1R,3S)-6-chloro-3-phenylindan-1-yl)-1,2,2-trimethylpiperazinium hydrogen malonate precipitates. The suspension in cooled to room temperature before the precipitate is isolated by centrifugation. The supernatant is discarded and the precipitate is washed with 2-propanol (5 ml). The slurry is centrifuged and the supernatant is discarded and the precipitate is dried "in vacuo" at 50° C. Yield: 0.98 grams (84%). Elemental analysis conforms to the structure. The X-ray diffractogram conforms to the diffractogram of the hydrogen malonate as shown in FIG. 3.

Synthesis of (I), Salt Formation of (VII) in Order to Remove cis Diastereoisomer of (VII), and Formation of the Hydrogen Succinate Salt from Crude (I)

Example 10

Synthesis of trans-1-((1R,3S)-6-chloro-3-phenylindan-1-yl)-3,3-dimethylpiperazinium (VII) Hydrogen Maleate Examples 2 and 5 are repeated, giving crude trans-1-((1R,3S)-6-chloro-3-phenylindan-1-yl)-3,3-dimethylpiperazine (VII) (ca. 20 grams) as an oil, which is further purified by flash chromatography on silicagel (eluent: ethyl acetate/ethanol/triethylamine 90:5:5) followed by evaporation to dryness on a rotary evaporator. Yield 12 grams of the title compound as an oil (cis/trans ratio, 90:10 according to NMR). The oil is dissolved in ethanol (100 ml), and to this solution is added a solution of maleic acid in ethanol to pH 3. The resulting mixture is stirred at room temperature for 16 hours, and the formed precipitate is collected by filtration. The volume of ethanol is reduced and another batch of precipitate is collected.

Yield 3.5 gram solid of the title compound (no cis isomer is detected according to NMR). Melting point 175-178° C.

Example 11 trans-1-((1R,3S)-6-chloro-3-phenylindan-1-yl)-3,3-dimethylpiperazine (VII)

A mixture of trans-1-((1R,3S)-6-chloro-3-phenylindan-1-yl)-3,3-dimethylpiperazinium hydrogen maleate (VII) (9.9 grams), concentrated aqueous ammonia (100 ml), brine (150 ml) and ethyl acetate (250 ml) is stirred at room temperature for 30 min. The phases are separated, and the aqueous phase is extracted with ethyl acetate once more. The combined organic phases are washed with brine, dried over magnesium sulphate, filtered and evaporated to dryness in vacuo. Yield 7.5 grams of oil.

Example 12

Preparation of trans-4-((1R,3S)-6-chloro-3-phenylindan-1-yl)-1,2,2-trimethylpiperazine Free Base (I)

Trans-1-((1R,3S)-6-chloro-3-phenylindan-1-yl)-3,3-dimethylpiperazine (8.9 grams) (VII) is dissolved in formic acid (10.5 ml) and to the solution is added formaldehyde (10.5 ml). Heated to 60° C. and kept at this temperature for 2½ hours. After cooling of the reaction mixture, water (50 ml) and hexane (50 ml) are added. Adjustment of pH with NaOH (27%, 33 ml) to pH>12. The hexane phase is washed with aq. NaCl (20 ml) and water (20 ml). Hexane is exchanged azeotropic with acetone (90 ml) and the mixture is concentrated. The crude free base in acetone (10 ml) is used without further purification.

Example 13

Trans-4-((1R,3S)-6-chloro-3-phenylindan-1-yl)-1,2,2-trimethylpiperazinium (I) Hydrogen Succinate Crude trans-4-((1R,3S)-6-chloro-3-phenylindan-1-yl)-1,2,2-trimethylpiperazine (I) in acetone solution (10 ml). A suspension of succinic acid (3.4 grams) in acetone (20 ml) is prepared and the trans-4-((1R,3S)-6-chloro-3-phenylindan-1-yl)-1,2,2-trimethylpiperazine (I) solution is added and the mixture is heated to reflux (55° C.). The succinic acid dissolves and during cooling of the solution trans-4-((1R,3S)-6-chloro-3-phenylindan-1-yl)-1,2,2-trimethylpiperazinium (I) hydrogen succinate starts precipitating. Suspension left overnight to precipitate. Trans-4-((1R,3S)-6-chloro-3-phenylindan-1-yl)-1,2,2-trimethylpiperazinium hydrogen succinate is isolated by filtration and washed with acetone (20 ml). The product is dried "in vacuo" at 60° C.

Yield: 7.9 grams.

Differential Scanning Calorimetry shows an endotherm with an onset temperature of 140° C. and a peak at 141° C. corresponding to the alpha form. XRPD diffractogram conforms with the alpha form. $[\alpha]_D^{20}=22.04°$ (c=1.0, methanol).

Synthesis of I using 1,2,2-trimethylpiperazine

Example 14

Synthesis of 3,3,4-trimethylpiperazin-2-one 3,3-dimethylpiperazin-2-one (50 grams) is suspended in 1,2-dimethoxyethane (DME) (150 ml) and potassium carbonate (70 grams) is added. Methyl iodide (66.4 grams) is added during half an hour, while the mixture is cooled slightly, allowing the temperature to reach 50° C. The mixture is stirred 9 hours at an oil bath at 40-45° C., and a sample is withdrawn for NMR, which indicates, that there is still 8% starting material left (signal at 2.8 ppm). More methyl iodide is added (4.6 grams), and the mixture is stirred for another 2½ hour at 40° C., and a new NMR sample shows full conversion. The mixture is filtered, and the filter cake is washed with DME. The filtrate is evaporated to dryness giving 41 grams of the title compound. NMR complies with the structure.

Example 15

Synthesis of 1,2,2-trimethylpiperazine

A solution of lithium aluminium hydride in tetrahydrofuran (THF) (1.0 M, Aldrich cat. no. 21,277-6, 90 ml) is heated to 50° C. on an oil batch. Crude 3,3,4-trimethylpiperazin-2-one (10 g) is suspended in THF and is slowly added, giving evolution of gas. The resulting mixture is stirred at 45-56° C. for 4 hours, giving full conversion to the title compound according to NMR (no signal at 1.2 ppm from starting material). The mixture is cooled, and water (3.3 ml) is added, giving evolution of gas. Then a solution of sodium hydroxide in water (15%, 3.3 ml) is added, giving more gas, and finally water (10 ml) is added. The mixture is filtered, and the filter cake is washed with THF (100 ml). The filtrates are concentrated on a rotary evaporator (0.3 atm. and 60° C. in the water batch). The residue is dissolved in THF (200 ml) and dried with sodium sulphate, then the mixture is filtered, and the filtrate is concentrated on a rotary evaporator (0.2 atm and 60° C. in the water batch) giving 6.4 grams of the title compound. NMR complies with the structure, the substance contains some THF.

Example 16

Synthesis of trans-4-((1R,3S)-6-chloro-3-phenylindan-1-yl)-1,2,2-trimethylpiperazinium (I) Hydrogen Fumarate from Compound VI Cis-(1S,3S)-3,5-dichloro-1-phenylindan (VI with LG=Cl) (17.8 grams) is coupled with distilled 1,2,2-trimethylpiperazine (VIII) (8.7 grams), using the procedure described in example 5. The raw product of the free amine (15.7 grams), containing 6% of the cis isomer, is used to form the hydrogen fumarate salt, using the procedure in example 6. Yield 15.7 grams of the title compound; NMR complies with the structure, no cis isomer is observed.

Synthesis of crystalline beta form of Compound I hydrogen succinate salt

Example 17

Synthesis of trans-4-((1R,3S)-6-chloro-3-phenylindan-1-yl)-1,2,2-trimethyl-piperazinium (I) Hydrogen Succinate, Beta Form Compound I hydrogen succinate (50 mg) is suspended in of water (1 ml) and allowed to equilibrate for 3 days. Any undissolved material is removed by filtration. The beta-form of Compound I hydrogen succinate forms during the natural evaporation of the solvent. The beta form is analysed after full evaporation of the solvent by XRPD and DSC.

Analytical results: Differential Scanning Calorimetry (DSC) shows an endotherm with an onset temperature of 135.6° C. and a peak at 137.5° C. corresponding to the beta form. XRPD conforms with the beta-form.

Characterisation of the Salts

Example 18

Solubility of the Salts of the Compound of Formula (I)

The solubility of the salts in water was determined by adding an excess (50 mg) of salt to 2 ml of water. The suspensions were left at the rotarmix for at least 24 hours, and subsequently pH was measured and the concentration was determined by HPLC. The solid precipitate was isolated and left to dry in the laboratory. The results are summarized in table 1.

TABLE 1

Solubility of the salts in water at room temperature.

| Sample | pH | Solubility(mg/ml) |
|---|---|---|
| Succinate 1:1 alpha | 4.4 | 13 |
| Malonate 1:1 | 3.9 | 15 |
| Fumarate | 3.8 | 1.5 |

Example 19

Stability of the Salts of the Compound of Formula (I)

The stability of the salts was investigated under the following circumstances: Heat, 60° C./80%RH: Samples were stored at 60° C. with 80%RH for one week. Then they were dissolved and analysed by BPLC.

Heat, 90° C.: Samples (~10 mg) were stored at 90° C. in closed containers containing 1 droplet of water. Then they were dissolved and analysed by HPLC.

Light: Samples were placed in the light cabinet at 250 w/m$^2$ for 24 hours. Then they were dissolved and analysed by HPLC.

The area of peaks in the chromatograms besides the peaks corresponding to the substance or the acid was summarized. The succinate salt of the invention does not show any degradation at all.

TABLE 2

| | Sum of impurity peak area % | | |
|---|---|---|---|
| Sample | 60° C./80% RH | 90° C. | Light |
| Malonate 1:1 alpha | 0 | 6.19 | 0.06 |
| Succinate 1:1 | 0 | 0 | 0 |
| Fumarate | 0.07 | 0.09 | 0.06 |

Example 20

The Hygroscopicity of Salts of the Compound of Formula (I)

The hygroscopicity of the fumarate salt, the succinate salt (the alpha form) and the malonate salt was investigated by Dynamic Vapour sorption (DVS). The fumarate and the succinate salts were found to be non-hygroscopic. The malonate absorbs gradually up to 1% of water when the relative humidity is raised to 95%, but with no hysteresis.

The invention claimed is:

1. A crystalline hydrogen succinate salt of the compound of formula (I):

2. The crystalline hydrogen succinate salt of claim 1, wherein the salt comprises an alpha crystal form characterized by one or more of:
    a. an X-Ray powder diffractogram obtained using CuK$_{\alpha 1}$ radiation ($\lambda$=1.5406 Å) that has main peaks at the following 2θ-angles: 9.36; 10.23; 11.81; 13.45; 16.21; 16.57; 17.49; 18.89; 19.20; 19.63; 20.01; 20.30; 21.15; 21.53; 21.93; 22.34; 24.37; 25.34; 27.27; and 29.65;
    b. an X-Ray powder diffractogram as shown in FIG. 1; and
    c. a Differential Scanning Calorimetry (DSC) trace that shows an endotherm with an onset temperature from 139-141° C.

3. A pharmaceutical composition comprising the crystalline hydrogen succinate salt of claim 1 and at least one pharmaceutically acceptable carrier, filler or diluent.

4. A method of treating a subject suffering from a disease or disorder comprising administering to the subject a therapeutically effective amount of the crystalline hydrogen succinate salt of claim 1, wherein the disease or disorder is selected from the group consisting of an anxiety disorder, depression, schizophrenia, Schizophreniform Disorder, Schizoaffective Disorder, Delusional Disorder, Brief Psychotic Disorder, Shared Psychotic Disorder and mania in bipolar disorder.

5. The method of claim 4, wherein the disease or disorder is Schizophrenia.

6. The method of claim 5, wherein the schizophrenia comprises positive symptoms, negative symptoms, depressive symptoms, or a combination thereof.

7. The method of claim 4, wherein the disease or disorder is selected from the group consisting of Schizophreniform Disorder, Schizoaffective Disorder, Delusional Disorder, Brief Psychotic Disorder, Shared Psychotic Disorder and mania in bipolar disorder.

8. The crystalline hydrogen succinate salt of claim 1, wherein the salt comprises a beta crystal form characterized by one or more of:
   a. an X-Ray powder diffractogram obtained using $CuK_{\alpha 1}$ radiation ($\lambda$=1.5406 Å) that has main peaks at the following 2θ-angles: 8.1; 10.5; 11.4; 14.0; 14.6; 15.6; 15.7; 16.2; 17.2; 17.5; 17.9; 18.4; 18.9; 19.2; 20.3; 21.0; 21.9; 22.5; 23.3; and 26.3;
   b. an X-Ray powder diffractogram as shown in FIG. 2; and
   c. a Differential Scanning Calorimetry (DSC) trace that shows an endotherm with an onset temperature from 135-138° C.

9. The pharmaceutical composition of claim 3, wherein the salt comprises an alpha crystal form characterized by one or more of:
   a. an X-Ray powder diffractogram obtained using $CuK_{\alpha 1}$ radiation ($\lambda$=1.5406 Å) that has main peaks at the following 2θ-angles: 9.36; 10.23; 11.81; 13.45; 16.21; 16.57; 17.49; 18.89; 19.20; 19.63; 20.01; 20.30; 21.15; 21.53; 21.93; 22.34; 24.37; 25.34; 27.27; and 29.65;
   b. an X-Ray powder diffractogram as shown in FIG. 1; and
   c. a Differential Scanning Calorimetry (DSC) trace that shows an endotherm with an onset temperature from 139-141° C.

10. The pharmaceutical composition of claim 3, wherein the salt comprises a beta crystal form characterized by one or more of:
    a. an X-Ray powder diffractogram obtained using $CuK_{\alpha 1}$ radiation ($\lambda$=1.5406 Å) that has main peaks at the following 2θ-angles: 8.1; 10.5; 11.4; 14.0; 14.6; 15.6; 15.7; 16.2; 17.2; 17.5; 17.9; 18.4; 18.9; 19.2; 20.3; 21.0; 21.9; 22.5; 23.3; and 26.3;
    b. an X-Ray powder diffractogram as shown in FIG. 2; and
    c. a Differential Scanning Calorimetry (DSC) trace that shows an endotherm with an onset temperature from 135-138° C.

11. The method of claim 4, wherein the salt comprises an alpha crystal form characterized by one or more of:
    a. an X-Ray powder diffractogram obtained using $CuK_{\alpha 1}$ radiation ($\lambda$=1.5406 Å) that has main peaks at the following 2θ-angles: 9.36; 10.23; 11.81; 13.45; 16.21; 16.57; 17.49; 18.89; 19.20; 19.63; 20.01; 20.30; 21.15; 21.53; 21.93; 22.34; 24.37; 25.34; 27.27; and 29.65;
    b. an X-Ray powder diffractogram as shown in FIG. 1; and
    c. Differential Scanning Calorimetry (DSC) trace that shows an endotherm with an onset temperature from 139-141° C.

12. The method of claim 4, wherein the salt comprises a beta crystal form characterized by one or more of:
    a. an X-Ray powder diffractogram obtained using $CuK_{\alpha 1}$ radiation ($\lambda$=1.5406 Å) that has main peaks at the following 2θ-angles: 8.1; 10.5; 11.4; 14.0; 14.6; 15.6; 15.7; 16.2; 17.2; 17.5; 17.9; 18.4; 18.9; 19.2; 20.3; 21.0; 21.9; 22.5; 23.3; and 26.3;
    b. an X-Ray powder diffractogram as shown in FIG. 2; and
    c. a Differential Scanning Calorimetry (DSC) trace that shows an endotherm with an onset temperature from 135-138° C.

* * * * *

UNITED STATES PATENT AND TRADEMARK OFFICE
CERTIFICATE OF CORRECTION

PATENT NO.       : 7,767,683 B2                                                Page 1 of 1
APPLICATION NO.  : 10/568572
DATED            : August 3, 2010
INVENTOR(S)      : Heidi Lopez de Diego It is certified that error appears in the above-identified patent and that said Letters Patent is hereby corrected as shown below:

On the title page item (75), Inventor line 3, "Ringgard" should be changed to --Ringgaard--.

Signed and Sealed this

Twenty-third Day of November, 2010

David J. Kappos
*Director of the United States Patent and Trademark Office*